United States Patent [19]

Ohno et al.

[11] Patent Number: 5,345,015
[45] Date of Patent: Sep. 6, 1994

[54] PROCESS FOR PRODUCING 1,1,2-TETRAFLUOROETHANE

[75] Inventors: Hiromoto Ohno; Makoto Miyamura, both of Kanagawa; Tatsuharu Arai, Tokyo; Kazuo Muramaki; Toshio Ohi, both of Kanagawa, all of Japan

[73] Assignee: Showa Denko K.K., Tokyo, Japan

[21] Appl. No.: 90,314

[22] Filed: Jul. 13, 1993

[30] Foreign Application Priority Data

Aug. 5, 1992 [JP] Japan .................................. 4-209187

[51] Int. Cl.$^5$ ............................................ C07C 17/08
[52] U.S. Cl. .................................... 570/164; 570/169
[58] Field of Search ............................. 570/164, 169

[56] References Cited

U.S. PATENT DOCUMENTS 3,709,800 1/1973 Fox ....................................... 570/164
4,975,156 12/1990 Wismer .............................. 570/164

FOREIGN PATENT DOCUMENTS 0446869 9/1991 European Pat. Off. .
3294237 12/1991 Japan .................................. 570/164
901297 7/1962 United Kingdom ................ 570/169

*Primary Examiner*—Alan Siegel
*Attorney, Agent, or Firm*—Sughrue, Mion, Zinn, Macpeak & Seas

[57] ABSTRACT

A process for producing 1,1,1-tetrafluoroethane from trichloroethylene and HF, which comprises introducing products of a reaction of trichloroethylene with HF, and products of a reaction of 1,1,1-trifluoro-2-chloroethane with HF into a first distillation column either separately or as a mixture thereof, recovering HCl as a distillate from the top of the first distillation column, and introducing the remainder into a second distillation column.

4 Claims, 3 Drawing Sheets

PROCESS FOR PRODUCING 1,1,2-TETRAFLUOROETHANE

FIELD OF THE INVENTION

The present invention relates to a process for the production of 1,1,1-tetrafluoroethane (hereinafter referred to as "$CF_3$—$CH_2F$" or "HFC-134a") in which HFC-134a can be produced efficiently by reacting trichloroethylene (hereinafter referred to as "$CHCl=CCl_2$" or "trichlene") with HF using simple equipment.

BACKGROUND OF THE INVENTION

In a conventionally known process for producing HFC-134a, trichlene is reacted with HF. The process is not accomplished in a single step, but effected by a two-step reaction in which the respective steps use different reaction conditions. This process comprises a first step reaction for reacting trichlene with HF to form 1,1,1-trifluoro-2-chloroethane (hereinafter referred to as "$CF_3$—$CH_2Cl$" or "HCFC-133a") and a second step reaction for reacting the HCFC-133a with HF to form HFC-134a.

The first step reaction represented by the following scheme (1):

is carried out, for example, under conditions of a pressure of 4 kg/cm²G, a temperature of 250° C., and an HF/trichlene molar ratio of 6/1.

The second step reaction represented by the following scheme (2):

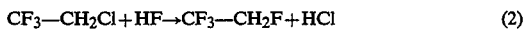

is carried out, for example, under conditions of a pressure of 4 kg/cm²G, a temperature of 350° C., and an HF/HCFC-133a molar ratio of 4/1.

In consequence, the prior art process comprises the steps of conducting the first step reaction under the above-described conditions, purifying the product to separate the HCl, re-adjusting the reaction conditions, conducting the second step reaction to yield HFC-134a, and then purifying and recovering the HFC-134a. This process has had a disadvantage that the distillation and separation steps are time-consuming, resulting in poor energy efficiency, due to the two reactions conducted under different conditions and each requiring its own distillation/separation step.

SUMMARY OF THE INVENTION

An object of the present invention is to provide a simplified process for producing HFC-134a through reaction of trichloroethylene with HF, which comprises:

reacting trichloroethylene with HF in a first reactor to form HCFC-133a, reacting HCFC-133a with HF in a second reactor to form HFC-134a, introducing the products from the first and second reactors into a first distillation column either separately or as a mixture thereof, recovering HCl as a distillate from the top of the first distillation column, and introducing the remainder into a second distillation column to obtain 1,1,2-tetrafluoroethane.

DETAILED DESCRIPTION OF THE INVENTION

Figure 1:
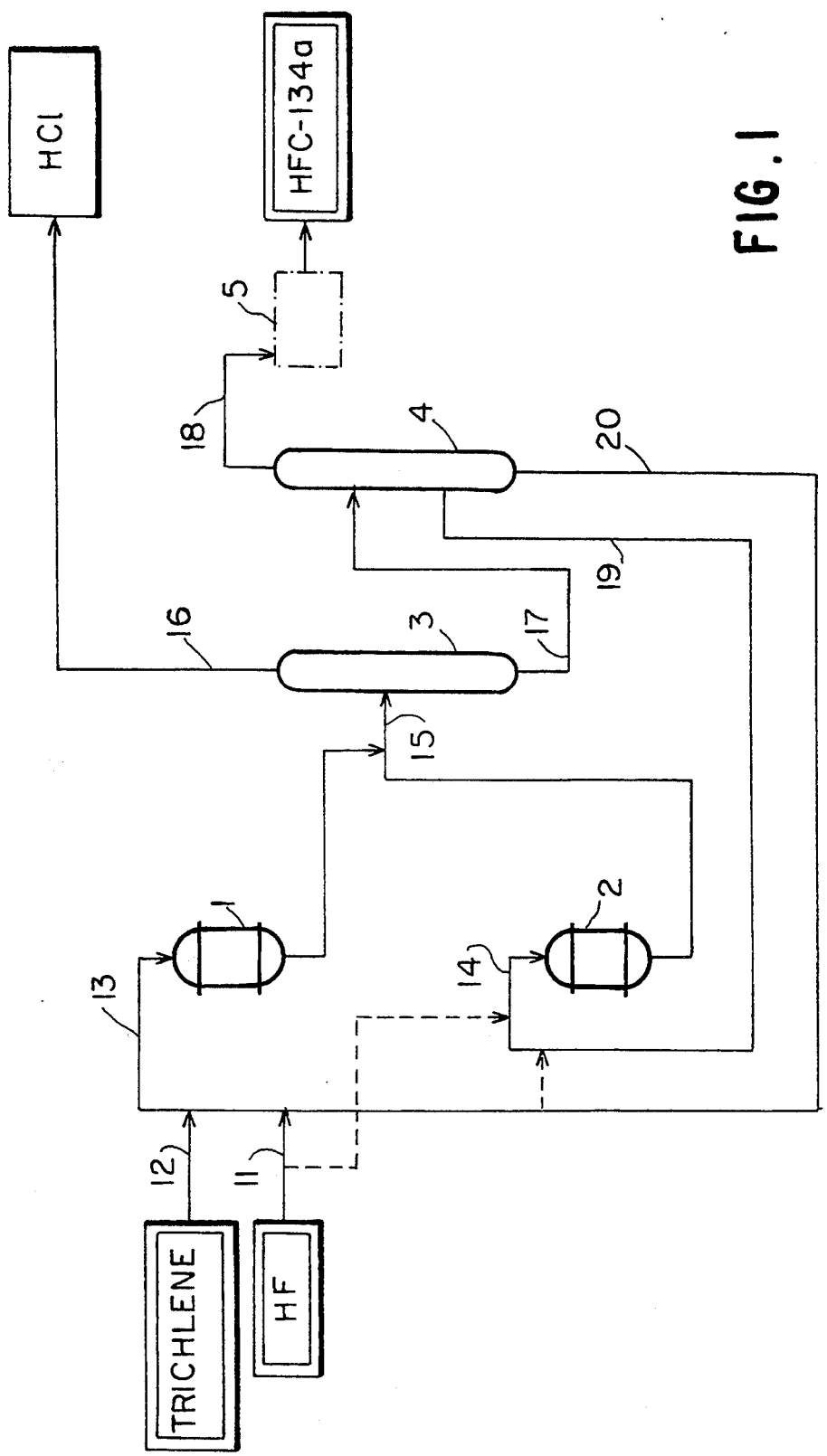
FIG. 1 is a flow sheet illustrating one embodiment of the present invention.

One referred embodiment of the process of the present invention comprises reacting trichloroethylene with HF in a first reactor to form HCFC-133a, reacting HCFC-133a with HF in a second reactor to form HFC-134a, introducing the products from the first and second reactors into a first distillation column to separate the products into a column top distillate comprising HCl and a bottom liquid containing HFC-134a, HCFC-133a, and HF as main components and a small amount of trichloroethylene, and introducing the bottom liquid into a second distillation column to separate it into (i) a column top distillate comprising HFC-134a containing small amounts of HCFC-133a and HF, (ii) a side-cut fraction containing HCFC-133a and HF as main components, and (iii) a bottom liquid containing HF as a main component and a small amount of trichloroethylene. The term "side-cut fraction" herein used means a fraction discharged from a portion of the second distillation column located above the bottom portion but below the portion at which the first column bottom liquid is introduced.

The second distillation column top distillate is introduced into a separately arranged purification step to recover the HFC-134a. The second distillation column side-cut fraction is fed to the second reactor while the bottom liquid is fed to the first reactor. If desired, the side-cut fraction may be mixed with HF to adjust their molar ratio before it is fed to the second reactor, and the bottom liquid may also be mixed with trichloroethylene and HF to adjust their molar ratio before it is fed to the first reactor.

The presence of HCl which has a very high specific volatility makes it difficult to operate distillation to separate HFC-134a, HCFC-133a and HF. According to the process of the present invention, however, HCl is eliminated from the top of the first distillation column so that the subsequent distillation(s) for separation of HFC-134a, HCFC-133a and HF can be stably and effectively conducted.

In another embodiment of the process, the above-described side-cutting in the second distillation column is not conducted and the first column bottom liquid introduced into the second distillation column is separated into (i) a second column top distillate containing HFC-134a as a main component and small amounts of HCFC-133a, HF, etc. and (ii) a bottom liquid containing HCFC-133a and HF as main components and a small amount of trichloroethylene. The column top distillate is introduced into a separately arranged purification step to recover the HFC-134a. On the other hand, the bottom liquid is introduced into a third distillation column to separate it into a column top distillate containing HCFC-133a as a main component and further containing HF and a bottom liquid containing a small amount of trichloroethylene, and the column top distillate is fed to the second reactor (after HF is added thereto and their molar ratio is adjusted if desired), while the bottom liquid is fed to the first reactor (after trichloroethylene and HF are added thereto and their molar ratio and amounts are adjusted if desired).

In still another embodiment which also does not conduct the side-cutting, the first column bottom liquid introduced into the second distillation column is separated into a column top distillate containing HFC-134a, HCFC-133a, and HF as main components and a bottom liquid containing HF as a main component and a small amount of trichloroethylene. The column top distillate is introduced into a third distillation column to separate it into a column top distillate containing HFC-134a as a main component and small amounts of HCFC-133a, HF, etc. and a bottom liquid containing HCFC-133a as a main component and further containing HF, and the third distillation column top distillate is introduced into a separately arranged purification step to recover the HFC-134a. The second distillation column bottom liquid is fed to the first reactor (after trichloroethylene and HF are added thereto and their molar ratio and amounts are adjusted if desired), while the third distillation column bottom liquid is fed to the second reactor (after HF is added thereto and their molar ratio is adjusted if desired).

FIG. 1 is a flow sheet showing one embodiment of the process of the present invention for producing HFC-134a. In FIG. 1, numeral 1 denotes a first reactor and 2 denotes a second reactor.

The reaction in first reactor 1 may be carried out under a pressure of from 0 to 6 kg/cm$^2$G, preferably from 0 to 4 kg/cm$^2$G at a temperature of from 200° to 350° C., preferably from 250° to 300° C. with the HF/trichloroethylene mol ratio of from 4/1 to 20/1, preferably from 6/1 to 10/1, for example, under a pressure of 4 kg/cm$^2$G, at a temperature of 250° C. and with an HF/trichloroethylene mol ratio of 6/1. The reaction in second reactor 2 may be carried out under a pressure of from 0 to 6 kg/cm$^2$G, preferably from 0 to 4 kg/cm$^2$G, at a temperature of from 300° to 380° C., preferably from 300° to 360° C. with the HF/HCFC-133a mol ratio of from 2/1 to 10/1, preferably from 4/1 to 8/1, for example, under a pressure of 4 kg/cm$^2$G, at a temperature of 350° C. and with an HF/HCFC 133a mol ratio of 4/1.

Reaction products from the first and second reactors are introduced as reaction products 15, either separately or as a mixture thereof, into first distillation column 3.

In the first distillation column, reaction products 15 are separated into first column top distillate 16 and first column bottom liquid 17. First column top distillate 16, which contains HCl as a main component, is put to other use. First column bottom liquid 17, which contains HFC-134a, HCFC-133a, and HF as main components and a small amount of trichloroethylene, is introduced into second distillation column 4.

The first distillation is generally carried out under the following conditions: pressure of from 2 to 10 kg/cm$^2$G, preferably from 4 to 6 kg/cm$^2$G; top temperature of from −65° to −30° C. preferably from −52° to −43° C.; bottom temperature of from 25° to 68° C., preferably from 41° to 52° C.; and relux ratio of from 10 to 30, preferably from 14 to 20.

In the second distillation column, first column bottom liquid 17 is separated into second column top distillate 18, second column side-cut fraction 19, and second column bottom liquid 20. Second column top distillate 18, which comprises HFC-134a containing small amounts of HCFC-133a, HF, etc., is introduced into a separately arranged purification step 5 to recover the HFC-134a. The HCFC-133a and HF contained in second column top distillate 18 are separated in this step and optionally used as feed material 13 for 14 for the first or second reactor, respectively. Purification step 5 may be conducted using another distillation column.

Second column side-cut fraction 19, which contains HCFC-133a and HF as main components, is fed as feed material 14 to the second reactor after HF is added thereto and their molar ratio is adjusted. Second column bottom liquid 20 consists mainly of HF containing a small amount of trichloroethylene. Although a part of the bottom liquid may be used for the adjustment of the feed material for the second reactor, most of the bottom liquid is used as feed material 13 for the first reactor after fresh HF and trichloroethylene are added thereto and their molar ratio and amounts are adjusted.

The second distillation is generally carried out under the following conditions: pressure of from 2 to 10 kg/cm$^2$G, preferably from 4 to 6 kg/cm$^2$G; top temperature of from 2° to 43° C., preferably from 16° to 27° C.; temperature at side-cut portion of from 25° to 67° C., preferably from 41° to 52° C.; bottom temperature of from 54° to 100° C., preferably from 71° to 84° C.; and reflux ratio of from 5 to 20, preferably from 8 to 15.

Numerals 11 and 12 denote HF and trichloroethylene, respectively, to be introduced into the system.

Due to the above-described construction of the equipment for the present invention, the products from the first and second reactors are introduced, either separately or as a mixture thereof, into the distillation columns, i.e., the first and second distillation columns, where they are separated into HFC-134a as the desired product, HCl as a by-product, an HF fraction containing a small amount of trichloroethylene usable for feed material adjustment, and a side-cut fraction to be used as a feed material for the second reactor. These fractions are subjected to the reaction and distillation/separation steps in combination with fresh trichloroethylene and HF as supplementary materials. Therefore, HFC-134a can be produced efficiently using a small number of apparatuses.

Figure 2:
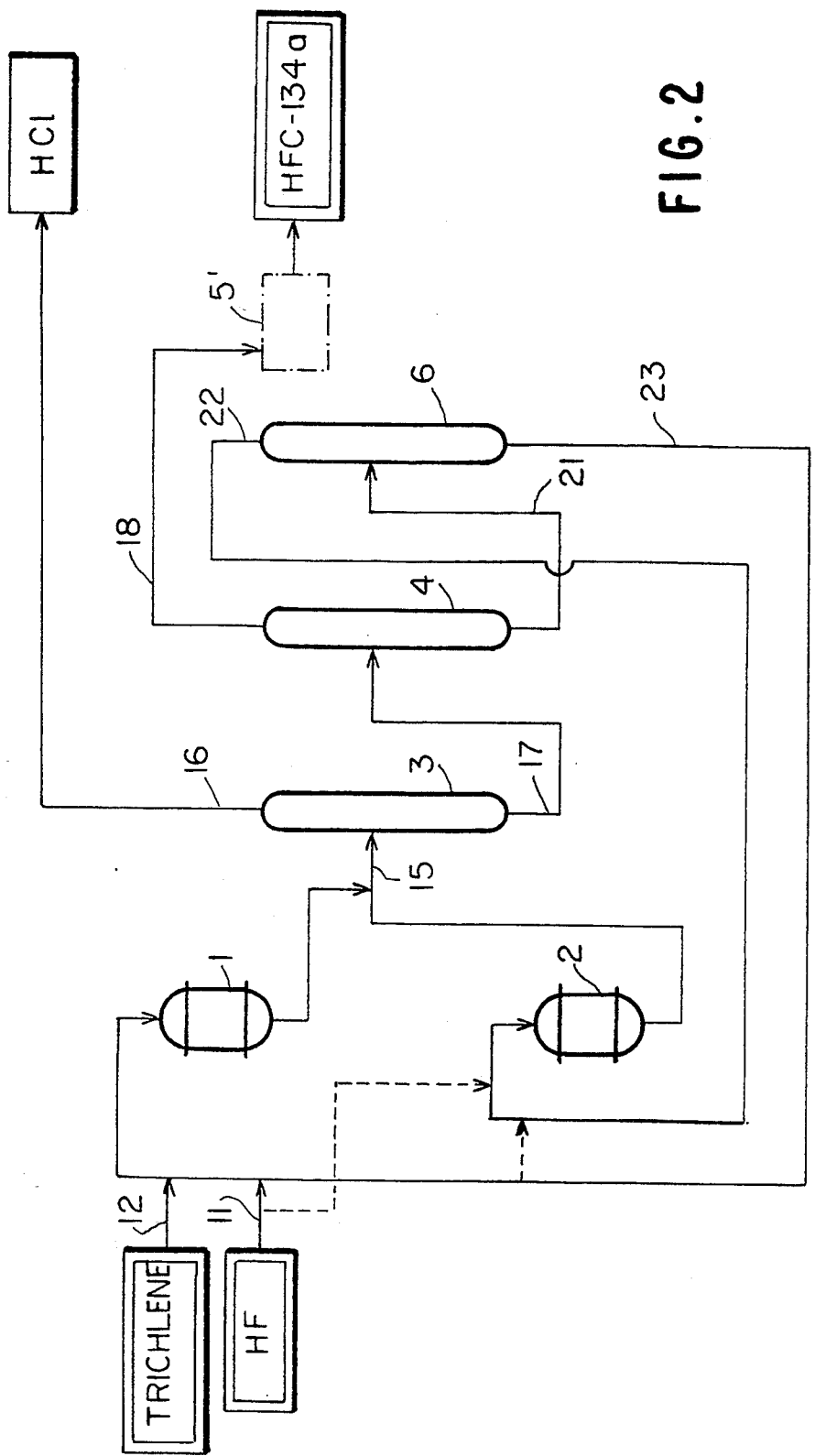
FIG. 2 is a flow sheet illustrating another embodiment in which side-cutting is not employed and one additional distillation column is used.
Figure 3:
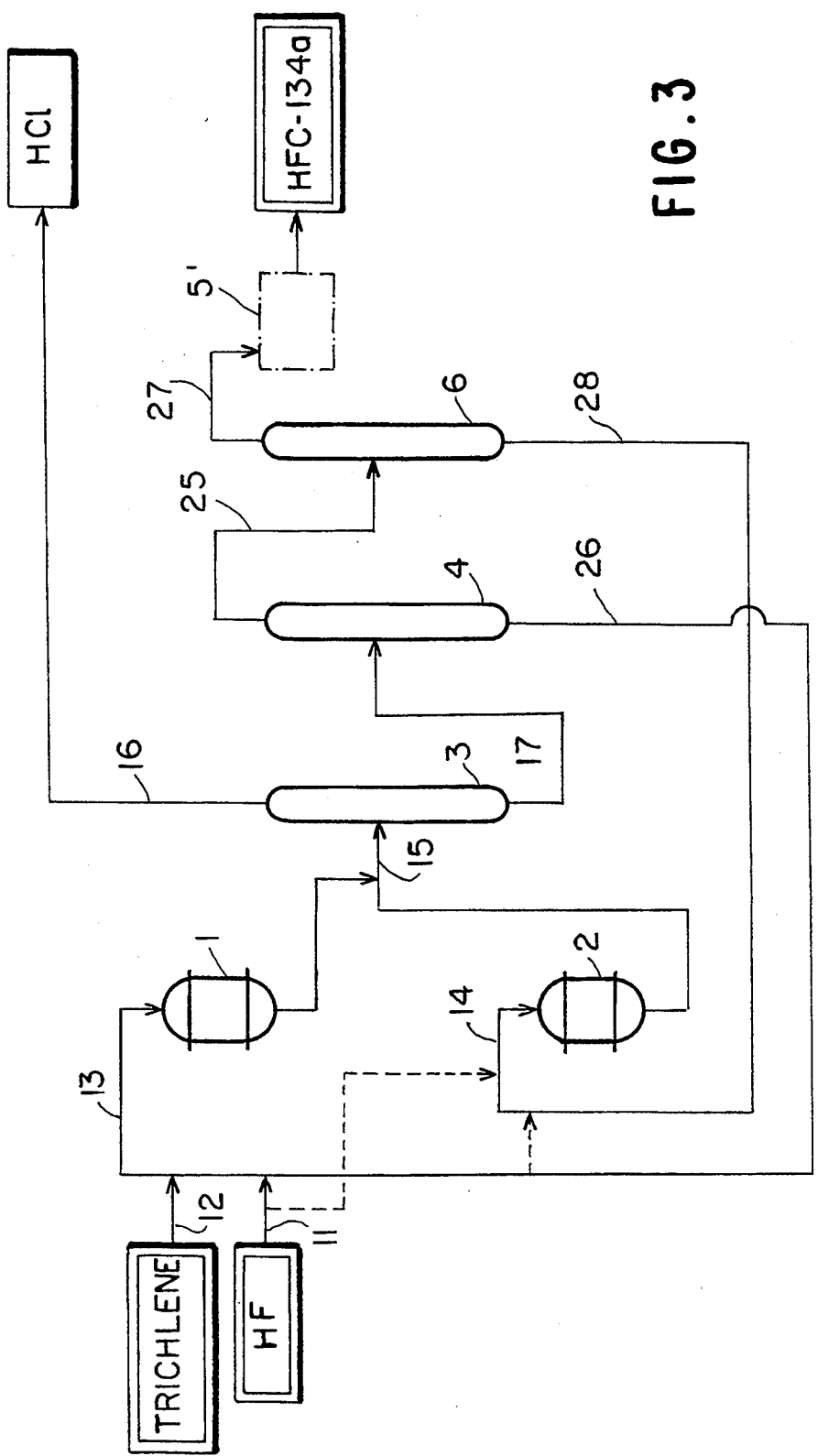
FIG. 3 is a flow sheet illustrating still another embodiment in which side-cutting is not employed and one additional distillation column is used.

FIGS. 2 and 3 illustrate the other embodiments of the present invention, in both of which side-cutting is not conducted in the second distillation column.

In the embodiment of FIG. 2, an HFC-134a fraction containing small amounts of HCFC-133a, HF, etc. is taken out from the top of the second distillation column, while the remainder is drawn off from the bottom and introduced into a third distillation column where a fraction consisting mainly of HCFC-133a containing HF is taken out from the top and a liquid consisting mainly of HF containing a small amount of trichloroethylene is drawn off from the bottom.

In this embodiment, the second distillation conditions are the same as those in the previous embodiment and the third distillation conditions are: pressure of from 2 to 10 kg/cm$^2$G, preferably from 4 to 6 kg/cm$^2$G; top temperature of from 25° to 67° C., preferably from 41° to 52° C.; bottom temperature of from 54° to 100° C., preferably from 71° to 84° C.; and reflux ratio of from 0.5 to 10, preferably from 1.5 to 5.

In the embodiment of FIG. 3, a liquid consisting mainly of HF containing a small amount of trichloroethylene is drawn off from the bottom of the second distillation column, while the remainder is taken out from the top and introduced into a third distillation column where an HFC-134a fraction containing small amounts of HCFC-133a, HF, etc. is taken out from the top and a liquid consisting mainly of HCFC-133a containing HF is drawn off from the bottom.

In this embodiment, the second distillation conditions are: pressure of from 2 to 10 kg/cm$^2$G, preferably from 4 to 6 kg/cm$^2$G; top temperature of from 25° to 67° C., preferably from 41° to 52° C.; bottom temperature of from 54° to 100° C., preferably from 71° to 84° C.; and reflux ratio of from 0 to 10, preferably from 0 to 5. The third distillation conditions are: pressure of from 2 to 10 kg/cm$^2$G, preferably from 4 to 6 kg/cm$^2$G; top temperature of from 2° to 43° C., preferably from 16° to 27° C.; bottom temperature of from 25° to 67° C. preferably from 41° to 52° C.; and reflux ratio of from 5 to 20, preferably from 8 to 15.

In FIG. 2 and 3, numeral 6 denote a third distillation column; 21 a second distillation column bottom liquid; 22 a third distillation column top distillate; 23 a third distillation column bottom liquid; 25 a second distillation column top distillate; 26 a second distillation column bottom liquid; 27 a third distillation column top distillate; 28 a third distillation column bottom liquid; and 5' a purification step, for example, using another distillation column and/or involving a purification treatment as described in U.S. patent application Ser. No. 08/056783 filed May 4, 1993.

ducted in accordance with the flow sheets shown in FIGS. 1 to 3. In these Examples, the component amounts in each part are given in terms of percent by weight, and the flow rate of each component in each part is shown as a relative value with the flow rate of the reaction products discharged from the first and second reactors and to be introduced into the first distillation column either separately or as a mixture thereof being taken as 100.

EXAMPLE 1

A test run was conducted in accordance with the flow sheet of FIG. 1. The results obtained are shown in Table 1, in which the Nos. correspond to the respective numerals in FIG. 1.

TABLE 1

|  | Component | 11 | 12 | 13 | 14 | 15 | 16 | 17 | 18 | 19 | 20 |
| --- | --- | --- | --- | --- | --- | --- | --- | --- | --- | --- | --- |
| Flow Rate: | HFC-134a | — | — | — | — | 8.8 | — | 8.8 | 8.8 | — | — |
|  | HCFC-133a | — | — | — | 44.1 | 44.8 | — | 44.8 | 0.8 | 44.0 | — |
|  | HF | 7.2 | — | 11.1 | 29.7 | 33.8 | — | 33.8 | 0.2 | 7.5 | 26.1 |
|  | HCl | — | — | — | — | 8.7 | 8.7 | — | — | — | — |
|  | Trichlene | — | 11.6 | 12.2 | 0.8 | 1.4 | — | 1.4 | — | — | 1.4 |
|  | Others | — | — | 0.2 | 1.8 | 2.5 | — | 2.5 | 0.5 | 0.9 | 1.1 |
|  | Total | 7.2 | 11.6 | 23.5 | 76.4 | 100 | 8.7 | 91.3 | 10.3 | 52.4 | 28.6 |
| Component | HFC-134A | — | — | — | — | 8.8 | — | 9.64 | 85.44 | — | — |
| Proportion: | HCFC-133a | — | — | — | 57.72 | 44.8 | — | 49.07 | 7.77 | 83.97 | — |
| by weight (%) | HF | 100 | — | 47.23 | 38.87 | 33.8 | — | 37.02 | 1.94 | 14.31 | 91.25 |
|  | HCl | — | — | — | — | 8.7 | 100 | — | — | — | — |
|  | Trichlene | — | 100 | 51.92 | 1.05 | 1.4 | — | 1.53 | — | — | 4.90 |
|  | Others | — | — | 0.85 | 2.36 | 2.5 | — | 2.74 | 4.85 | 1.72 | 3.85 |
|  | Total | 100 | 100 | 100 | 100 | 100 | 100 | 100 | 100 | 100 | 100 |

As evident from Table 1, the reaction products introduced either separately or as a mixture thereof are separated by the two distillation columns, and the feed materials for the first and second reactors are adjusted by combining these fractions with supplementary trichlene and HF, while the by-product HCl is recovered and the desired HFC-134a is concentrated.

EXAMPLE 2

A test run was conducted in accordance with the flow sheet of FIG. 2. The results obtained are shown in Table 2, in which the Nos. correspond to the respective numerals in FIG. 2.

TABLE 2

|  | Component | 11 | 12 | 13 | 14 | 15 | 16 | 17 | 18 | 21 | 22 | 23 |
| --- | --- | --- | --- | --- | --- | --- | --- | --- | --- | --- | --- | --- |
| Flow Rate: | HFC-134a | — | — | — | — | 8.8 | — | 8.8 | 8.8 | — | — | — |
|  | HCFC-133a | — | — | — | 44.1 | 44.8 | — | 44.8 | 0.8 | 44.0 | 44.0 | — |
|  | HF | 7.2 | — | 11.1 | 29.7 | 33.8 | — | 33.8 | 0.2 | 33.6 | 7.5 | 26.1 |
|  | HCl | — | — | — | — | 8.7 | 8.7 | — | — | — | — | — |
|  | Trichlene | — | 11.6 | 12.2 | 0.8 | 1.4 | — | 1.4 | — | 1.4 | — | 1.4 |
|  | Others | — | — | 0.2 | 1.8 | 2.5 | — | 2.5 | 0.5 | 2.0 | 0.9 | 1.1 |
|  | Total | 7.2 | 11.6 | 23.5 | 76.4 | 100 | 8.7 | 91.3 | 10.3 | 81.0 | 52.4 | 28.6 |
| Component | HFC-134A | — | — | — | — | 8.8 | — | 9.64 | 85.44 | — | — | — |
| Proportion: | HCFC-133a | — | — | — | 57.72 | 44.8 | — | 49.07 | 7.77 | 54.32 | — | — |
| by weight (%) | HF | 100 | — | 47.23 | 38.87 | 33.8 | — | 37.02 | 1.94 | 41.48 | 83.97 | 91.25 |
|  | HCl | — | — | — | — | 8.7 | 100 | — | — | — | 14.31 | — |
|  | Trichlene | — | 100 | 51.92 | 1.05 | 1.4 | — | 1.53 | — | 1.73 | — | 4.90 |
|  | Others | — | — | 0.85 | 2.36 | 2.5 | — | 2.74 | 4.85 | 2.47 | 1.72 | 3.85 |
|  | Total | 100 | 100 | 100 | 100 | 100 | 100 | 100 | 100 | 100 | 100 | 100 |

Although the embodiments shown in FIGS. 2 and 3 each additionally necessitates the third distillation column, the stability of operation is improved because of elimination of the side-cutting in the second distillation column.

The present invention is explained in more detail with reference to the following Examples which were con-

EXAMPLE 3

A test run was conducted in accordance with the flow sheet of FIG. 3. The results obtained are shown in Table 3, in which the Nos. correspond to the respective numerals in FIG. 3.

TABLE 3

|  | Component | 11 | 12 | 13 | 14 | 15 | 16 | 17 | 25 | 26 | 27 | 28 |
|---|---|---|---|---|---|---|---|---|---|---|---|---|
| Flow Rate: | HFC-134a | — | — | — | — | 8.8 | — | 8.8 | 8.8 | — | 8.8 | — |
|  | HCFC-133a | — | — | — | 44.1 | 44.8 | — | 44.8 | 44.8 | — | 0.8 | 44.0 |
|  | HF | 7.2 | — | 11.1 | 29.7 | 33.8 | — | 33.8 | 7.7 | 26.1 | 0.2 | 7.5 |
|  | HCl | — | — | — | — | 8.7 | 8.7 | — | — | — | — | — |
|  | Trichlene | — | 11.6 | 12.2 | 0.8 | 1.4 | — | 1.4 | — | 1.4 | — | — |
|  | Others | — | — | 0.2 | 1.8 | 2.5 | — | 2.5 | 1.4 | 1.1 | 0.5 | 0.9 |
|  | Total | 7.2 | 11.6 | 23.5 | 76.4 | 100 | 8.7 | 91.3 | 62.7 | 28.6 | 10.3 | 52.4 |
| Component | HFC-134a | — | — | — | — | 8.8 | — | 9.64 | 14.04 | — | 85.44 | — |
| Proportion: | HCFC-133a | — | — | — | 57.72 | 44.8 | — | 49.07 | 71.45 | — | 7.77 | 83.97 |
| by weight (%) | HF | 100 | — | 47.23 | 38.87 | 33.8 | — | 37.02 | 12.28 | 91.25 | 1.94 | 14.31 |
|  | HCl | — | — | — | — | 8.7 | 100 | — | — | — | — | — |
|  | Trichlene | — | 100 | 51.92 | 1.05 | 1.4 | — | 1.53 | — | 4.90 | — | — |
|  | Others | — | — | 0.85 | 2.36 | 2.5 | — | 2.74 | 2.23 | 3.85 | 4.85 | 1.72 |
|  | Total | 100 | 100 | 100 | 100 | 100 | 100 | 100 | 100 | 100 | 100 | 100 |

As described above, in the HFC-134a production process of the present invention, reaction products from the first and second reactors are subjected together to distillation and separation either separately or as a mixture thereof and the feed materials for the reactors are adjusted by combining the resulting fractions with supplementary trichlene and HF, whereas in the prior art process, the reaction products from the first reactor and those from the second reactor are separately treated in respective distillation and separation steps and the feed materials for the reactors are adjusted by combining the resulting fractions with supplementary trichlene and HF. Because of the above-inventioned difference, the process of the invention has advantages in that the distillation step is simple and the energy unit is small.

While the invention has been described in detail and with reference to specific embodiments thereof, it will be apparent to one skilled in the art that various changes and modifications can be made therein without departing from the spirits and scope thereof.

What is claimed is:

1. A process for producing 1,1,1,2-tetrafluoroethane through reaction of trichloroethylene with HF, which comprises:
   reacting trichloroethylene with HF in a first reactor to form 1,1,1-trifluoro-2-chloroethane,
   reacting 1,1,1-trifluoro-2-chloroethane with HF in a second reactor to form 1,1,1,2-tetrafluoroethane,
   introducing the products from the first and second reactors into a first distillation column either separately or as a mixture thereof,
   recovering HCl as a distillate from the top of the first distillation column, and
   introducing the remainder into a second distillation column to obtain 1,1,1,2-tetrafluoroethane.

2. The process as claimed in claim 1, which comprises:
   introducing the products from the first and second reactors either separately or as a mixture thereof into the first distillation column to separate the products into a first column top distillate comprising HCl and a first column bottom liquid containing 1,1,1,2-tetrafluoroethane, 1,1,1-trifluoro-2-chloroethane, and HF as main components,
   introducing the first column bottom liquid into the second distillation column to separate the first column bottom liquid into (i) a second column top distillate comprising 1,1,1,2-tetrafluoroethane and small amounts of 1,1,1-trifluoro-2-chloroethane and HF, (ii) a second column side-cut fraction containing 1,1,1-trifluoro-2-chloroethane and HF as main components, and (iii) a second column bottom liquid containing HF as a main component,
   introducing the second column top distillate into a separately arranged purification step to recover 1,1,1,2-tetrafluoroethane,
   feeding the second column side-cut fraction to the second reactor for reaction, and
   feeding the second column bottom liquid to the first reactor for reaction.

3. The process as claimed in claim 1, which comprises:
   introducing the products from the first and second reactors either separately or as a mixture thereof into the first distillation column to separate the products into a first column top distillate comprising HCl and a first column bottom liquid containing 1,1,1,2-tetrafluoroethane, 1,1,1-trifluoro-2-chloroethane, and HF as main components,
   introducing the first column bottom liquid into the second distillation column to separate the first column bottom liquid into (i) a second column top distillate comprising 1,1,1,2-tetrafluoroethane and small amounts of 1,1,1-trifluoro-2-chloroethane and HF, and (ii) a second column bottom liquid containing 1,1,1-trifluoro-2-chloroethane and HF as main components,
   introducing the second column top distillate into a separately arranged purification step to recover 1,1,1,2-tetrafluoroethane,
   introducing the second column bottom liquid into a third distillation column,
   feeding a third column top distillate to the second reactor, and
   feeding a third column bottom liquid to the first reactor.

4. The process as claimed in claim 1, which comprises:
   introducing the products from the first and second reactors either separately or as a mixture thereof into the first distillation column to separate the products into a first column top distillate comprising HCl and a first column bottom liquid containing 1,1,1,2-tetrafluoroethane, 1,1,1-trifluoro-2-chloroethane, and HF as main components,
   introducing the first column bottom liquid into the second distillation column to separate the first column bottom liquid into (ii) a second column top distillate containing 1,1,1,2-tetrafluoroethane, 1,1,1-trifluoro-2chloroethane, and HF as main components and (ii) a second column bottoms liquid containing HF as a main component, introducing the second column top distillate into a third distillation column to separate the second column top distillate into (i) a third column top distillate and (ii) a third column bottom liquid containing 1,1,1-trifluoro-2-chloroethane as a main component, introducing the third column top distillate into a separately arranged purification step to recover 1,1,1,2-tetrafluoroethane, feeding the third column bottom liquid to the second reactor, and feeding the second column bottom liquid to the first reactor.

* * * * *